United States Patent
Unger et al.

(10) Patent No.: US 7,200,201 B2
(45) Date of Patent: Apr. 3, 2007

(54) FLAT PANEL DETECTOR BASED SLOT SCANNING CONFIGURATION

(75) Inventors: Christopher D. Unger, Brookfield, WI (US); David M. Hoffman, New Berlin, WI (US); Vivek Bhatt, Elm Groove, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/990,267

(22) Filed: Nov. 16, 2004

(65) Prior Publication Data

US 2006/0104415 A1    May 18, 2006

(51) Int. Cl.
 *G01N 23/04* (2006.01)
(52) U.S. Cl. ......................................... 378/62; 378/150
(58) Field of Classification Search ................ 378/149, 378/98.8, 145–148, 7, 37–38, 62, 87, 150, 378/116
See application file for complete search history.

(56) References Cited

U.S. PATENT DOCUMENTS

| | | | |
|---|---|---|---|
| 4,096,391 A | 6/1978 | Barnes ........................ 250/505 |
| 6,035,013 A * | 3/2000 | Orava et al. ................... 378/37 |
| 6,339,636 B1 * | 1/2002 | Ogawa ......................... 378/146 |
| 6,501,819 B2 | 12/2002 | Unger et al. ................... 378/5 |
| 6,795,527 B2 * | 9/2004 | Francke ...................... 378/146 |
| 2003/0095633 A1 * | 5/2003 | Van Woezik ................ 378/147 |
| 2003/0235265 A1 * | 12/2003 | Clinthorne et al. ............ 378/4 |

* cited by examiner

*Primary Examiner*—Edward J. Glick
*Assistant Examiner*—Hoon Song
(74) *Attorney, Agent, or Firm*—McAndrews, Held & Malloy, Ltd.; Peter J. Vogel; Michael A. Dellapenna

(57) ABSTRACT

The present invention relates to a diagnostic X-ray device, system or apparatus for performing diagnostic radiology and a method of configuring such a diagnostic X-ray device, system or apparatus. More specifically, the present invention relates to a diagnostic system for forming at least one image of an object having enhanced contrast. The system comprises a beam source adapted to produce an imaging beam and a masking member adapted to form at least one beam portion from the imaging beam and adapted to image the object. The system further comprises a flat panel detector positioned in a path of at least one beam portion penetrating the object and adapted to form at least one image of the object.

4 Claims, 9 Drawing Sheets

Scanning Motion

Scanning Motion

Scanning Motion

Scanning Motion

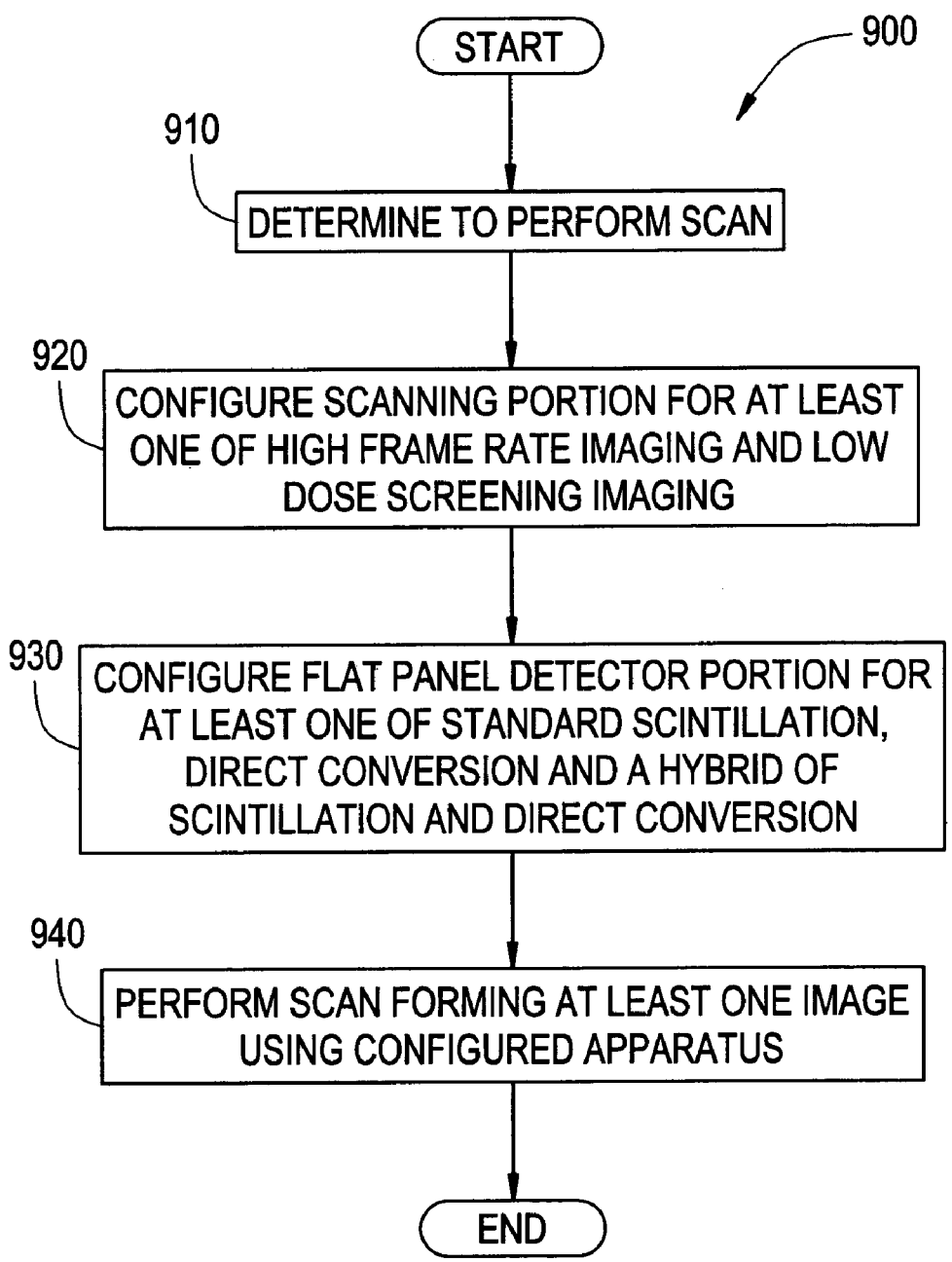

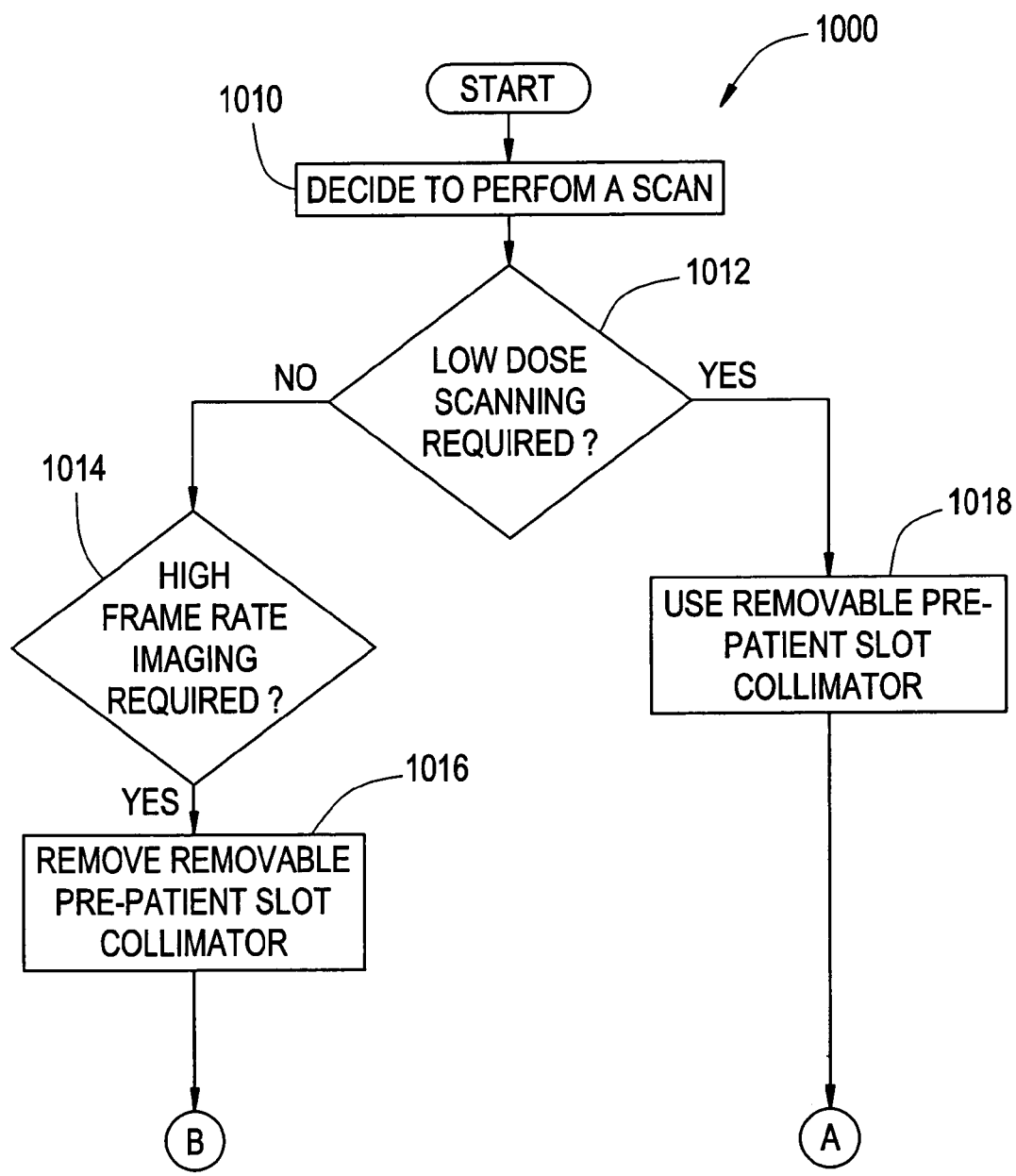

FLAT PANEL DETECTOR BASED SLOT SCANNING CONFIGURATION

BACKGROUND OF THE INVENTION

This application is directed in general to diagnostic radiology using an X-ray device, system or apparatus. This application is directed in particular to an X-ray device, system or apparatus using a flat panel detector in a slot scanning configuration.

It is known that scattered X-rays have contrast reducing effects. One of the most significant challenges in using standard flat panel imaging is that, after performing X-ray imaging of an object (a patient for example), the X-ray image is composed of more scattered X-rays than direct transmitted X-rays, thus reducing contrast. This is especially true for thick objects (i.e., heavy patients).

Efforts have been made to improve contrast in diagnostic image radiology systems, including using air gaps, improved electronics and certain forms of scanning techniques. However, such known techniques have generally proved to be unsatisfactory in obtaining high image quality while maintaining rapid scanning rates and low exposure times. While it is possible to obtain images of good quality with very slow scanning speeds, as with a single scanning beam for example, such low speed scanning techniques are not practical in diagnostic radiology in view of the fact that the patients' body parts and organs move while the patients are being X-rayed. For example, it should be appreciated that the abdomen is the most difficult portion of the body to accurately X-ray in view of its relatively dense concentration of organs, bones and body fluids.

Thus, if relatively long exposure times are required to obtain an X-ray image, the images may be blurred due to the movement of the organs and body parts being X-rayed and are useless for diagnostic purposes. One possible solution is to use a post-patient collimator to reduce or eliminate scatter. One limitation associated with previously used post-patient collimators is that they do not totally reduce or eliminate scattered radiation and may block X-rays that have passed through the patient, forming useful doses.

Other efforts have been made to reduce or eliminate X-ray scattering, including using different types of slot scanners (pre-patient slot scanners for example) with an image detector, where the radiation is blocked prior to passing through the patient. In such manner, only slots of radiation are passed through to impinge on the patient. The detector and pre-patient collimator are swept across the patient, the images are collected and pasted together to form a single image. It is contemplated that this type of slot scanner configuration may result in a 4–10× dose reduction. Increasing the slots reduces the total scan time.

One example of a previous effort to reduce or eliminate X-ray scattering is disclosed in U.S. Pat. No. 4,096,391 (the '409 patent), incorporated herein by reference in its entirety, which discloses a slot scanner configuration using film (a film cassette for example). The '409 patent discloses a multiple slot scanning method and apparatus. A conventional X-ray tube projects a continuous X-ray beam in the direction of a patient. As described, a fore slot plate is positioned in the path of the X-ray beam at a predetermined position above the patient. The fore slot plate includes a plurality of narrow slots which permit the passage of a group of narrow parallel beam segments for scanning the patient.

Upon striking the patient, the narrow beam segments are partially defused or scattered in any a number of arbitrary directions. These scattered beam portions carry no significant information, and thus tend to blur or reduce the contrast in any resulting X-ray image. On the other hand, portions of the beam segments or portions penetrate directly through the patient. It is these penetrating beam portions which carry information as to the structural configuration of the patient's internal organs.

In the abdominal area for example, extremely clear, high quality X-ray images are necessary to obtain the degree of detail required to permit accurate diagnosis of disease or the detection of tumors and other improper growths. However, due to the thickness, dense concentration of material in the abdomen, and the large radiation field necessary to image the abdominal area, a large amount of X-ray scattering is created, thus making it difficult to obtain clear radiographic images of the abdomen, as mentioned previously. Accordingly, it is highly desirable and important to the advancement of abdominal diagnostic radiography for example, that clearer X-ray images of this area of the body be obtained.

It should be appreciated that such previously used slot scanners or pre-patient collimators have limitations. They require a fixed source to image distance ("SID") (i.e., tube to detector). The materials used to detect the X-rays in the such previous designs (single crystal Si and Xe gas for example) do not work effectively for high kV imaging used for certain applications (radiography of R&F for example). Finally, the mechanical scanning used to form the image makes high frame rate imaging such as fluoro imaging difficult if not impossible.

One other known attempt to reduce or eliminate X-ray scattering includes using a slot scanner based on Xenon gas and avalanche detection. Still another attempt includes using a slot scanner based on single crystal Si sensors turned orthogonally to the X-ray incidence. While it is appreciated that both attempts may reduce X-ray scatter (due to the slot scanning) and photon counting, such attempts are generally only valid as scanned slot scanners.

BRIEF SUMMARY OF THE INVENTION

One embodiment relates in general to a diagnostic X-ray device, system or apparatus for performing diagnostic radiology and a method of configuring such a diagnostic X-ray device, system or apparatus. More specifically, one embodiment relates to a diagnostic system for forming at least one image of an object having enhanced contrast. The system comprises a beam source adapted to produce an imaging beam and a masking member adapted to form at least one beam portion from the imaging beam and adapted to image the object. The system further comprises a flat panel detector positioned in a path of at least one beam portion penetrating the object and adapted to form at least one image of the object.

In at least one embodiment, the masking member comprises at least one or more of a removable pre-patient collimator having at least one slot positioned in a path of the imaging beam; a post-patient collimator having at least one slot positioned in the path of the at least one beam portion penetrating the object and an X-ray collimator defining at least one slot therein.

Embodiments of the system comprise an X-ray system and the imaging beam comprises an X-ray beam. The system may have a table for supporting the object and a support adapted to maintain a ratio of the source to pre-patient collimator/source to constant image. Still other embodiments of the system comprise the flat panel detector which is adapted to measure scatter, provide for interconnections or measure scatter and provide for interconnections.

Yet another embodiment comprises a method of configuring a diagnostic system for forming at least one image of an object having enhancing contrast. In this embodiment, the method comprises configuring a scanning portion and a flat panel detector. Configuring the scanning portion comprises configuring for at least one of high frame rate imaging and low dose scanning imaging. Configuring the flat panel detector portion comprises configuring for at least one of standard scintillation, direct conversion and a hybrid of scintillation and direct conversion. This method comprises performing a scan of an object and forming an image using the configured system.

Still another embodiment comprises forming an image of an object using an X-ray device. This embodiment comprises producing an X-ray beam using a conventional X-ray source and creating a plurality of beam segments from the X-ray beam. The method further comprises scanning the object using at least one of the beam portion and producing an X-ray image on a flat panel detector. This method may comprises at least one of using a removable pre-patient collimator to form the plurality of beam portions and using a post-patient collimator passing at least one of the beam portion. Further, the method may comprise minimizing acquisition time.

BRIEF DESCRIPTION OF SEVERAL VIEWS OF THE DRAWINGS

FIG. 9 depicts a detailed high level flow diagram depicting a method of configuring a diagnostic radiology (X-ray) device, system or apparatus and forming at least one image using such configured system in accordance with certain embodiments of the present invention.

FIGS. 10A and 10B depict a detailed flow diagram depicting a method of configuring a diagnostic radiology (X-ray) device, system or apparatus and forming at least one image using such configured system in accordance with certain embodiments of the present invention.

Figure 1:
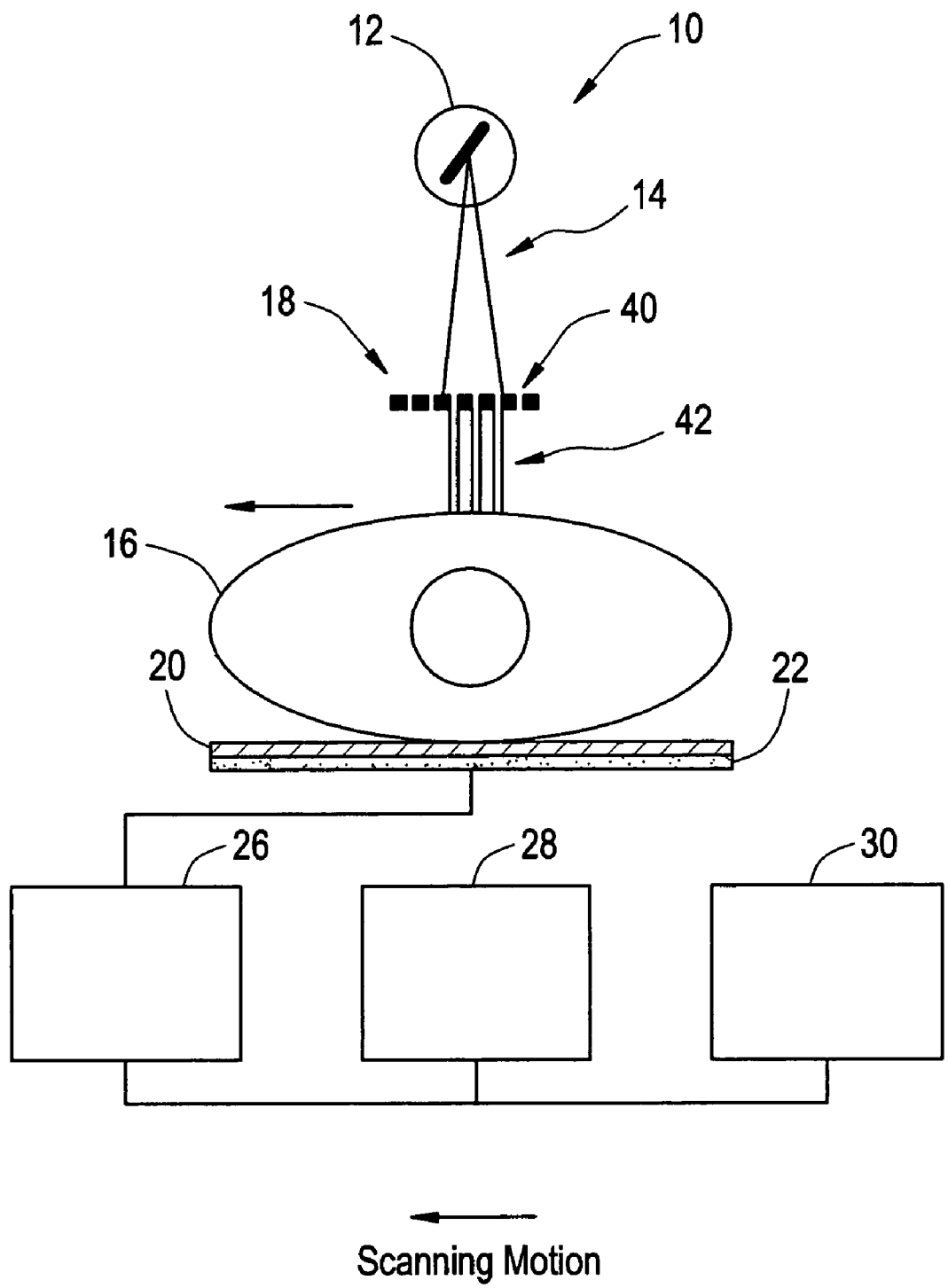
FIG. 1 depicts a schematic illustration of a diagnostic radiological (X-ray) device, system or apparatus in accordance with certain embodiments of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Clear, high quality X-ray images are necessary to obtain the degree of detail needed to permit accurate diagnosis of disease and detection of tumors and other improper growths in the crowded abdominal area, for example. However, due to the thickness and dense concentration of material in the abdomen, and the large radiation field necessary to image that area, a large amount of X-rays are scattered, thus making it difficult to obtain clear images, as provided previously. Accordingly, it is highly desirable and important to the advancement of diagnostic radiography (abdominal diagnostic radiography for example) that clear X-ray images (i.e., having enhanced contrast) be obtained.

At least one embodiment relates in general to configuring a diagnostic X-ray device, system or apparatus and performing diagnostic radiology using such a configured X-ray device, system or apparatus. More particularly, embodiments are directed to an X-ray device, system or apparatus having at least one of a standard X-ray collimator, a removable pre-patient slot collimator, a post-patient collimator and a flat panel detector. One embodiment is adapted to perform either high frame rate imaging (fluoro and tomo imaging for example) or low dose screening applications. Further, embodiments of the apparatus are adapted to obtain the benefits of low dose slot scanning for high KV applications ("RAD"). For the purpose of illustration only, the following detailed description references certain embodiments of an X-ray device, apparatus or system. However, it is understood that the embodiments may be used with other devices, apparatus or imaging systems.

In at least one embodiment, a pre-patient slot collimator is positioned in the device, system or apparatus such that the system is employed as a slot scanner. Further, the pre-patient collimator may be removable, such that the system may be used in slot scanner or full field of view (alternatively referred to as "FOV") modes. The slot scanner mode provides dose reduction benefits, while the full FOV mode provides fast image acquisitions (fluoro, tomo, cine, etc.). The flat panel detector may be a scintillator detector or direct conversion detector, the shaded areas of the detector behind the pre-patient collimator may be used as dead space for interconnections or as active pixels to measure scatter, or a hybrid thereof. In at least one embodiment, the post-patient collimator may be optimized to reject scatter between active pixel runs, but detect scatter in the shadowed pixels, enabling measurement of the scattered image. In at least one embodiment, the SID of this configuration may be modified as long as the ratio of source to pre-patient collimator/source to image remains constant. A mechanized support may be used to maintain the ratio as the SID is changed.

Referring now to the drawings, wherein like reference numerals designate identical or corresponding parts throughout the several views, and more particularly to FIG. 1 hereof, embodiments of the scanning apparatus and method are illustrated in schematic form. In at least one embodiment, the X-ray device, system or apparatus, generally designated 10, comprises at least one scanning and flat panel detector portions.

FIG. 1 depicts a conventional X-ray source 12 having a focal spot as indicated projecting an X-ray beam 14 (a continuous X-ray beam for example) in the direction of an object 16. Currently available X-ray sources have a focal spot size of about 2.0 millimeters or less (0.3 millimeters for example). It will be understood that the object being X-rayed may alternatively be referred to as a patient in view of the fact that at least one embodiment is viewed as being most beneficial in diagnostic radiology, although it should be appreciated that the embodiments may be used in radiographic studies of many different types of animate and inanimate objects in addition to human patients.

According to at least one embodiment, a first or removable masking member 18 (a pre-patient slot collimator for example) is positioned in the path of the X-ray beam 14 at a predetermined position above the patient 16. In at least one embodiment, the pre-patient slot 18 is formed of a material, or combination of materials, generally opaque to X-ray beams (lead, steel and tungsten for example) and includes at least two, but generally a plurality, of narrow slots 40 which permit the passage of at least two, but generally a plurality of, narrow beam segments or portions 42 for scanning the patient 16. It is contemplated that slots 40 may have a minimum dimension of at least two times (2×) the focal spot size of the conventional X-ray source 12 for example, although other dimensions and shapes are contemplated. It is contemplated that the masking member may further comprise a conventional field limiting diaphragm or standard X-ray collimator (best viewed in FIG. 4) positioned above, below or in place of the pre-patient collimator 18, limiting the total area of irradiation.

Figure 5:
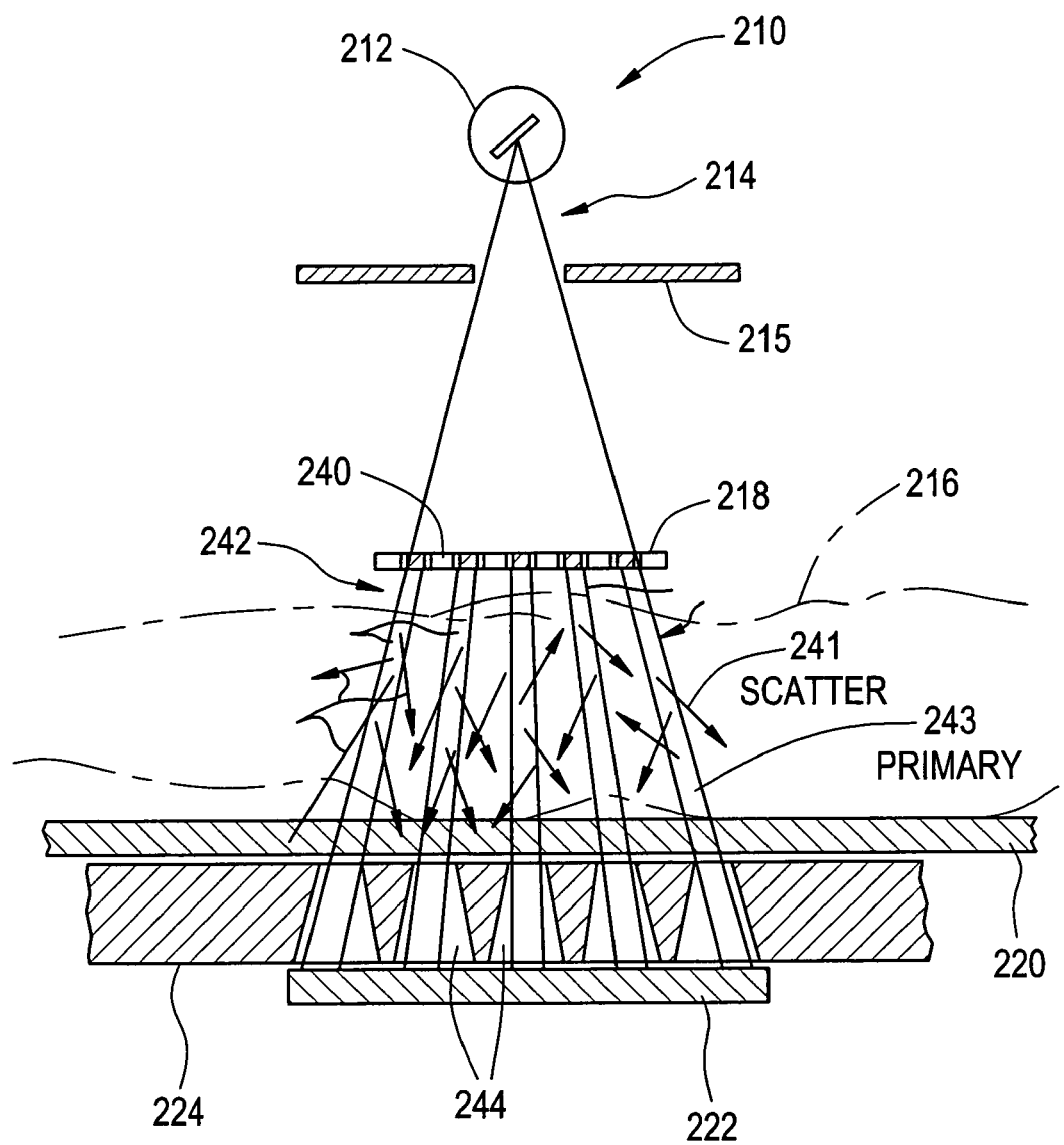
FIG. 5 depicts a partial side elevational view of a diagnostic radiological (X-ray) device, system or apparatus (similar to that in FIG. 3) including a side view of the pre- and post-patient collimators and flat panel detector in accordance with certain embodiments of the present invention.

Upon striking the patient 16, the one or more narrow beam segments or portions 42 are partially defused or scattered in any number of arbitrary directions (See FIG. 5 for example). These scattered beam portions carry no significant information, and thus tend to blur, reduce or otherwise affect the contrast in any resulting X-ray image. On the other hand, at least one but generally two or more of the beam segments or portions 42 penetrate directly through the patient 16. It is these penetrating beam segments or portions (alternatively referred to as "primary radiation") which carry the information regarding the structural configuration of the patient's internal organs.

Referring again to FIG. 1, patient 16 is shown supported by a table 20, which in at least one embodiment is constructed of an X-ray transparent material, with the flat panel detector 22 positioned beneath the table 20. A processor 26 (which is one embodiment, may include a control for X-ray source 12) is illustrated communicating with at least the flat panel detector 22. The processor 26 is adapted to receive, store and process the image having significantly enhanced contrast and clarity relative to previous known embodiments. In at least one embodiment, the apparatus 10 includes a video processor 28 and display 30, adapted to display the image having improved contrast and clarity (in real time for example). While the processor 26, video processor 28 and display 30 are shown communicating via a hardwired connection, other methods of communicating (wireless connections for example) are contemplated.

In operation, at least the pre-patient collimator 18 is moveable (using any suitable drive device), scanning a patient 16 using at least one but generally a plurality of beam segments or portions 42. In this manner, the flat panel detector 22 is scanned by those beam segments or portions 42 that penetrate the patient 22, resulting in a clear image which does not include any shadows or evidence of the existence of the pre-patient collimator 18. More importantly, the use of at least the pre-patient collimator 18 effectively attenuates most if not all scattered radiation, so that the image on the flat panel detector 22 has significantly improved contrast and clarity relative to images taken without using such a pre-patient collimator. While it is contemplated that, in at least one embodiment, the pre-patient collimator 18 moves alone or synchronously with the flat panel detector, in other embodiments, it is contemplated that the patient 16 and table 18 may move with respect to the pre-patient collimator 18 and the flat panel detector 22.

In at least one embodiment, the system 10 may include an arm or support pivoted about an axis which passes through the focal spot of the X-ray source 12. The pre-patient collimator 40 may be mounted to the support using a mounting means which may be formed integral with the support. In at least one embodiment, a post-patient collimator may be coupled to a base portion of the support (using pegs for example).

Linear motion of at least the pre- and/or post-patient collimator may be assured using a linear guide, for example to which the collimators are coupled by means of conventional roller bearings or other suitable coupling means which permit free linear motion with a minimum of friction. A conventional drive device (an electric motor for example) may be used to drive the support and pre- and post-patient collimators through a conventional worm gear drive for example. The worm gear drive includes a worm gear driven by the motor and engaging a gear segment. The worm gear drive and electric motor assembly are entirely conventional. The worm gear and electric drive assembly are suitable for use with the embodiments of present invention in view of the fact that the worm gear arrangement enables precision motion while electric power is normally conventionally available to energize the motor.

It is contemplated that many other types of drives and power sources, including hydraulic and belt arrangements may be used to power the system. Different types of drives may easily be adapted to the described system in view of the present teachings by those skilled in the art.

It is further contemplated that a switch may be used to energize the motor. When energized, the motor drives the support through the worm gear drive, causing the pre- and/or post-patient slot collimators to move. A start sensor, which may be a conventional limit switch, a photocell device, or any similar type of conventional device, may be used to detect movement of at least one of the collimators. The start sensor is coupled to an X-ray source control, which is in turn coupled to the X-ray source 12, for energizing source 12 when the start sensor is triggered. A conventional stop sensor, similar to the start sensor, may be coupled to the X-ray source control for shutting off the source 12 after the pre- and/or post-patient slot collimators have moved sufficiently to complete its scanning movement.

Figure 2:
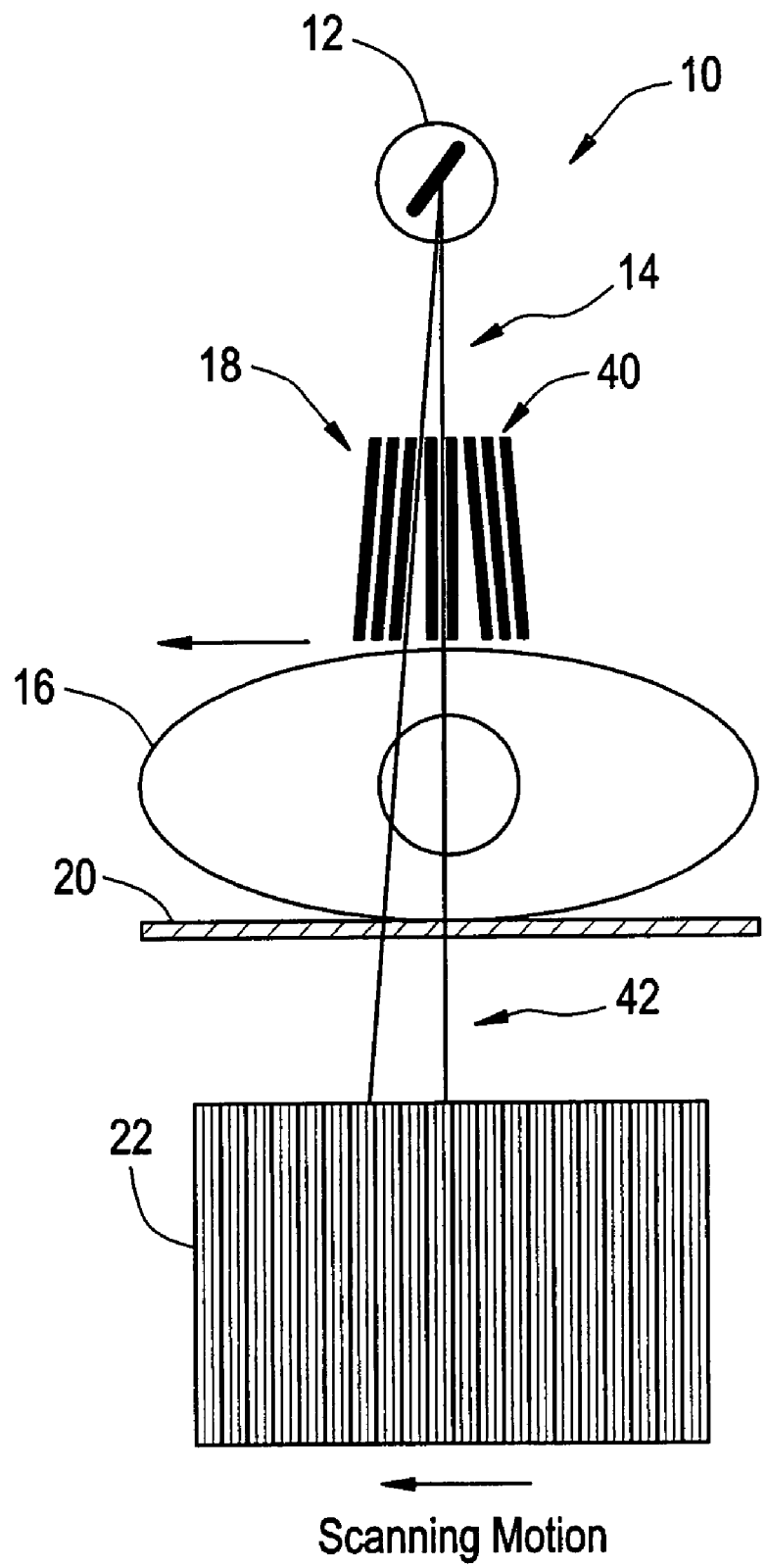
FIG. 2 depicts a schematic illustration of a diagnostic radiological (X-ray) device, system or apparatus (similar to that of FIG. 1) including a plan view of the pre-patient collimator and flat panel detector in accordance with certain embodiments of the present invention.

FIG. 2 depicts a schematic illustration of a diagnostic radiological (X-ray) device, system or apparatus (similar to that of FIG. 1) including a plan view of the pre-patient collimator and flat panel in accordance with certain embodiments of the present invention.

Similar to FIG. 1, the conventional X-ray source 12 having a focal spot as indicated, projects an X-ray beam 14 (a continuous X-ray beam for example) in the direction of patient 16. According to at least one embodiment of the present invention, the removable pre-patient collimator 18 is positioned in the path of the X-ray beam 14 at a predetermined position above the patient 16 and adapted to form one or more beam segments or portions 42 that penetrate the patient. The flat panel detector 22 is adapted to be scanned by those portions 42 that penetrate the patient.

Figure 6:
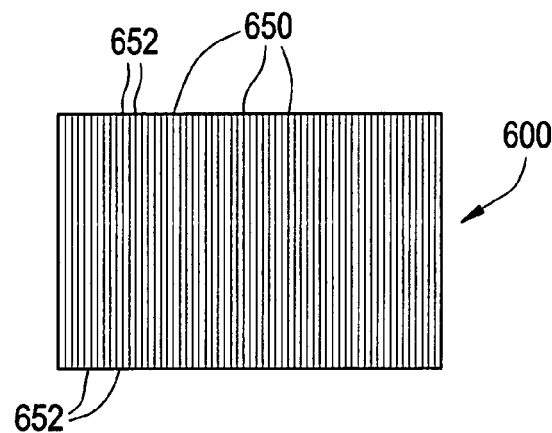
FIG. 6 depicts a scintillator or direct conversion flat panel detector having all lines active in accordance with certain embodiments of the present invention.

In one embodiment, the flat panel detector 22, similar to that depicted in FIG. 6, comprises at least a standard scintillator or direct conversion flat panel detector having one or more active lines. In at least one embodiment, one or more lines are adapted to detect direct radiation, while the other data lines are adapted to measure scatter (perhaps for diffraction or scatter imaging).

Figure 3:
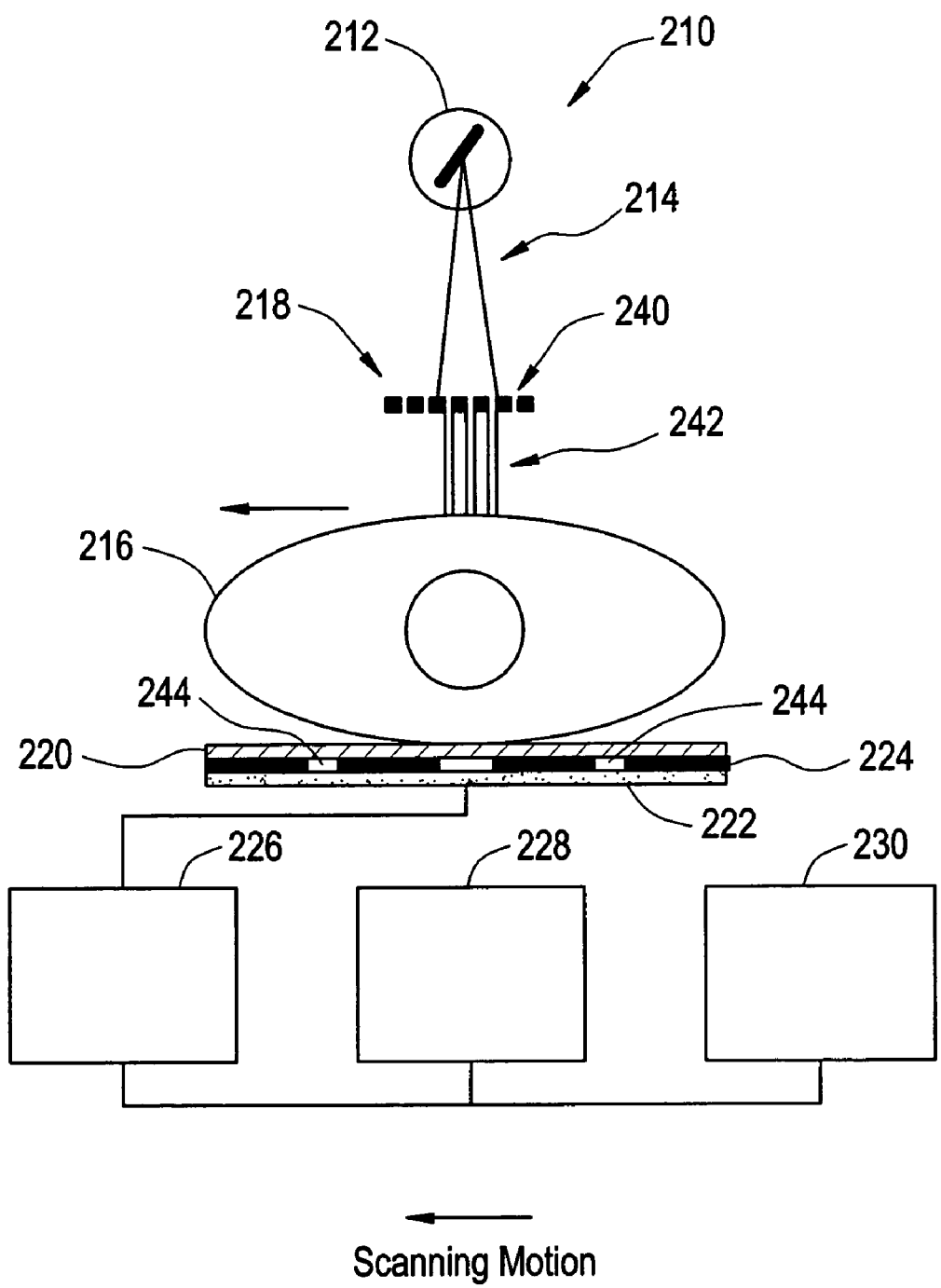
FIG. 3 depicts a schematic illustration of a diagnostic radiological (X-ray) device, system or apparatus (similar to that of FIG. 1) including a post-patent collimator in accordance with certain embodiments of the present invention.

FIG. 3 depicts a schematic illustration of a diagnostic radiological (X-ray) device, system or apparatus (similar to that of FIG. 1) including a post-patent collimator in accordance with certain embodiments of the present invention. FIG. 3 depicts a conventional X-ray source 212 having a focal spot as indicated projecting an X-ray beam 214 (a continuous X-ray beam for example) in the direction of a patient 216. Currently available X-ray sources have a focal spot size of about 2.0 millimeters or less (0.3 millimeters for example).

According to at least one embodiment, a removable pre-patient collimator 218 is positioned in the path of the X-ray beam 214 at a predetermined position above the patient 216. In at least one embodiment, a masking member (a removable pre-patient collimator for example) is formed of a material, or combination of materials, generally opaque to X-rays (lead, steel and tungsten for example) and includes at least two, but generally a plurality of, narrow slots 240 which permit the passage of at least two, but generally a plurality of, narrow parallel beam segments or portions 242 for scanning the patient 216. It is contemplated that slots 240 may have a minimum dimension of at least two times (2x) the focal spot size of the conventional X-ray source 212 although other dimensions and shapes are contemplated. It is further contemplated that the masking member may further comprise a conventional field limiting diaphragm or standard X-ray collimator positioned above, below or in place of the pre-patient collimator 218, limiting the total area of irradiation.

Upon striking the patient 216, the one or more narrow beam segments or portions 242 are partially defused or scattered in any number of arbitrary directions (best view in FIG. 5). These scattered beam portions carry no significant information, and thus tend to blur, reduce or otherwise affect the contrast in any resulting X-ray image. On the other hand, at least one but generally two or more, of the beam segments or portions 242 penetrate directly through the patient 216. It is these penetrating beam segments or portions (i.e., primary radiation) which carry the information regarding the structural configuration of the patient's internal organs.

Referring again to FIG. 3, patient 216 is shown supported by a table 220, which in at least one embodiment is constructed of an X-ray transparent material. In at least one embodiment, the masking member further comprises at least a post-patient collimator or aft slot plate 224 positioned beneath table 220 and above flat panel detector 222. In at least one embodiment, the post-patient collimator 224 is comprised of any suitable X-ray opaque material (the same or different material as the pre-patient collimator 218) and includes at least one, but generally a plurality of, slots 244 which permit the passage of at least one, but generally a plurality, of parallel beam segments for scanning.

As illustrated, the post-patient collimator 224 includes at least one, but generally a plurality of, slots 244 whose width is small in comparison to their depth and which are significantly wider than slots 240 in the pre-patient collimator 218 so that they are of sufficient width to accommodate those beam segments 242 which penetrate the patient 216. Both the pre- and post-patient collimators 218, 224 include an identical number of slots and are essentially congruent, although the post-patient collimator 224 is substantially expended in scale relative to the pre-patient collimator 218. Comparative dimensions of the pre- and post-patient collimators 218, 224 will be set forth subsequently.

In operation, the pre- and post-patient collimators 218, 224 are moved synchronously to effectively scan the patient 216 using various beam portions 242. In this manner, the flat panel detector 222 is scanned by the one or more beam segments or portions penetrating the patient 216, resulting in a clear image which does not include any shadows or evidence of the existence of the two slot collimators 218, 224. More importantly, the use of the collimators 218, 224 results in a very effective attenuation of virtually all scattered radiation so that the image on the flat panel detector 222 has significantly improved contrast and clarity relative to images taken without the combined collimators 218, 224.

A central processor 226 is illustrated communicating with at least the flat panel detector 222. The central processor 226 is adapted to receive, store and process one or more images having significantly improved contrast and clarity relative to previous known embodiments. In at least one embodiment, the system 210 includes a video processor 228 and display 230, adapted to display the one or more images having improved contrast and clarity (in real time for example). While the central processor 226, video processor 228 and display 230 are shown communicating via a hardwired connection, other methods of communicating (wireless connections for example) are contemplated.

Figure 4:
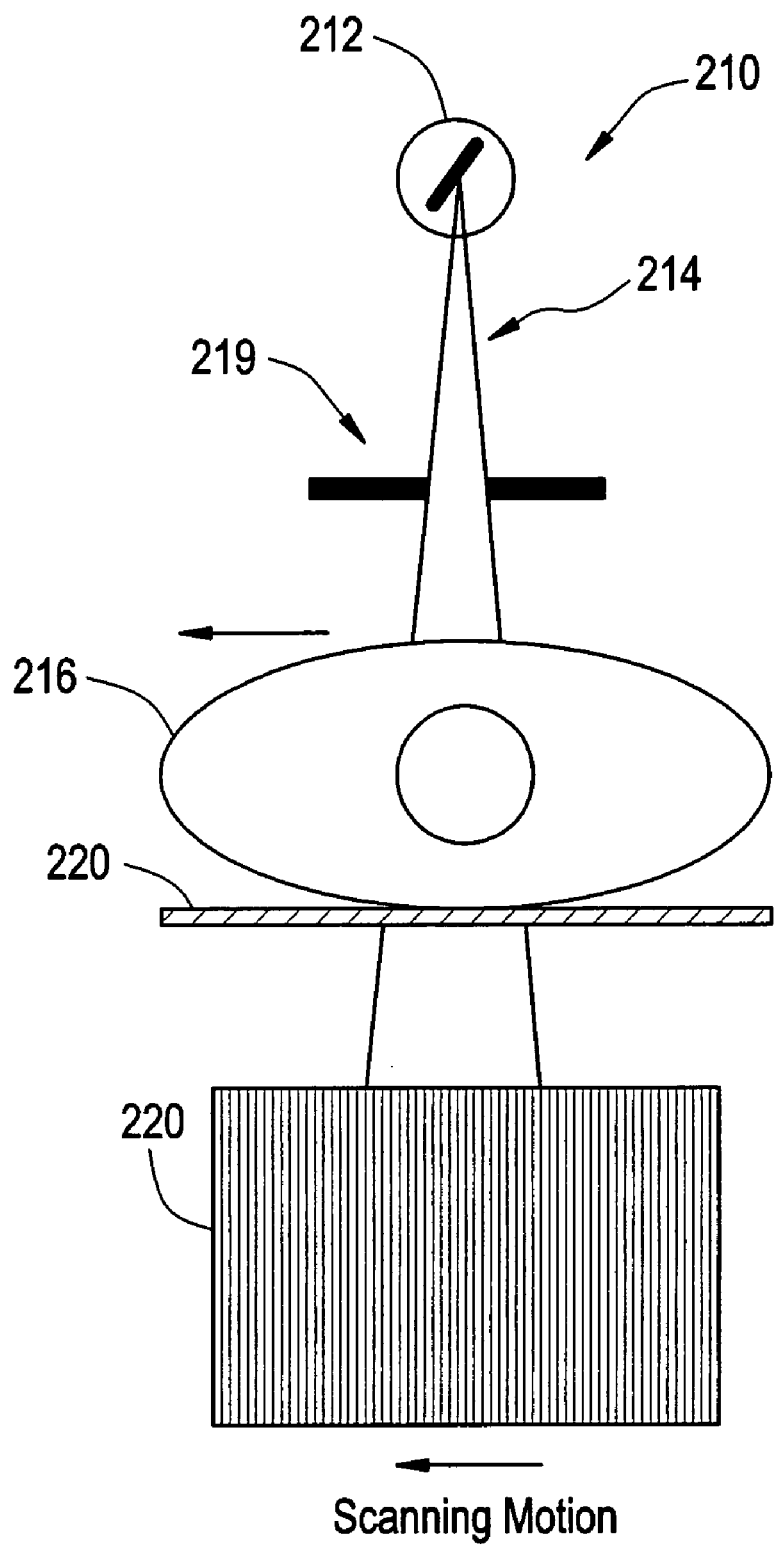
FIG. 4 depicts a schematic illustration of a diagnostic radiological (X-ray) device, system or apparatus (similar to that in FIG. 3) including a plan view of the post-patient collimator and flat panel detector in accordance with certain embodiment of the present invention.

FIG. 4 depicts a schematic illustration of a schematic illustration of a diagnostic radiological (X-ray) device, system or apparatus (similar to that of FIG. 3) including a plan view of the post-patient collimator and flat panel detector in accordance with certain embodiment of the present invention.

Upon striking the patient 216, the one or more narrow beam segments or portions 242 are partially defused or scattered in a number of arbitrary directions. These scattered beam portions carry no significant information, and thus tend to blur, reduce or otherwise affect the contrast in any resulting X-ray image. On the other hand, portions of the beam segments 242 (i.e., primary radiation) penetrate directly through the patient 216, and it is these penetrating beam portions which carry the information regarding the structural configuration of the patient's internal organs.

In at least one embodiment of the flat panel detector 222 of FIG. 4 (similar to that of FIG. 7) comprises at least two active lines separated at the frequency of the pre-patient collimator 240. The dead space between the active lines may be used for interconnections and packaging. This embodiment may be especially useful for detector rows comprised of single crystal direct conversion material. In this configuration, the areas between the primary detector rows may have one or more active rows to measure scatter.

As mentioned previously, exposure time is an important factor in obtaining clear X-ray images since involuntary movements of organs and the like can cause unacceptable image blurring if exposures are carried out over long intervals. In general, for abdominal examinations, the exposure time should be limited to approximately ½ second. Embodiments easily permit short scanning intervals of approximately ½ second or less.

FIG. 5 depicts a partial side elevational view of a diagnostic radiological (X-ray) device, system or apparatus 210 (similar to that of FIG. 3) comprising at least one scanning and flat panel detector portions. In at least one embodiment, the scanning portion comprises at least one masking member, which may include at least one of a standard X-ray collimator, a pre-patient collimator and a post-patient collimator.

In FIG. 5, the conventional X-ray source 212 projects a continuous X-ray beam 214 in the direction of patient 216. System 210 includes a removable, pre-patient collimator 218 placed at predetermined position above patient 216. Pre-patient collimator 216 includes at least one but generally a plurality of narrow slots 240 which permit the passage of a group of narrow parallel beam segments 242 for scanning the patient 216. A conventional field limiting diaphragm or X-ray collimator 215 is positioned above or below the pre-patient collimator 218 to limit the total area of irradiation in accordance with known practice.

Upon striking the patient 216, the narrow beam segments 242 are partially defused or scattered as indicated by a plurality of arrows 241 pointing in a number of arbitrary directions. These scattered beam portions 241 carry no significant information, and thus tend to blur or reduce the contrast in any resulting X-ray image. On the other hand, portions of the beam segments 242 penetrate directly through the patient 216, and it is these penetrating beam portions, known as primary radiation 243, which carry the information as to the structural configuration of the patient's internal organs.

Referring again to FIG. 5, the patient is shown supported by a table 220 which is constructed of a relatively light, X-ray transparent material. Beneath the table 220 a post-patient collimator 224 is positioned above the flat panel detector 222. The post-patient collimator 224 includes a plurality of slots 244 whose width is small compared to their depth and which are wider than the slots 240 in the pre-patient collimator 218 so that they are of sufficient width to accommodate the expanded beam segments 22 which penetrate the patient 216. The slots 244 preferably have a depth to width ratio of at least four to one. In one embodiment, both the pre- and post-patient collimators 218, 224 include an identical number of slots and are essentially congruent, although the post-patient collimator 224 is substantially expended in scale relative to the pre-patient collimator 219.

In operation, the pre- and post-patient collimators 218, 224 are moved synchronously to effectively cause a scanning of the patient 216 by the various beam segments 243. In this manner the flat panel detector 222 is scanned by at least one of the beam segments 243 penetrating the patient 216, resulting in a clear image which does not include any shadows or evidence of the existence of the collimators. More importantly the use of collimators results in a very effective attenuation of virtually all scattered radiation so that the image on the flat panel detector has a significantly improved contrast and clarity relative to images taken without the combined slit plate structure of the present invention.

Having described in detail embodiments of the present invention, one method of operation will now be summarized. A patient 216 is first placed in an appropriate position on the X-ray table 220. The system 210 is then started by switching on the motor. The start sensor activates the X-ray tube control to turn on the X-ray source 212 when motion of at least one of the pre- and post-patient collimator 218, 224 is detected. The stop sensor is subsequently activated by motion of at least one of the pre- and post-patient collimators 218, 224, whereupon the X-ray source 21 is shut off by the X-ray tube control. At least one of the pre- and post-patient collimators must move a minimum distance equal to the width of one slot plus the width of one slot separation, that is, a total distance of about 2.5 cm for example. Preferably, at least one of the pre- and post-patient collimators 218, 224 moves two or three times this distance (at least 5 cm for example) to assure a complete and uniform scanning of the patient 216. It is noted that at the minimum scanning speed of a 5 cm scan would be accomplished in about ½ second for example, the proper maximum exposure time for abdominal X-rays.

Additional improvements in image contrast may be obtained by increasing the depth of the slots in one or both of the collimators, increasing the separation between slots, having narrower slots or having a greater number of narrower slots spaced closer together. One or more embodiments of the system may be produced using one or more (a plurality for example) of square, rectangular, circular or other geometrically shaped apertures in place of the elongated slots in one or both of the collimators as shown. That is, each slot, in effect, would be replaced by one or more squares, rectangles, circles or other geometrical shapes and the neighboring multiplicity of apertures would be shifted in such a manner, that when the system is scanned across the patient, a uniform radiation exposure to the flat panel detector would result. However, such a system requires greater precision in manufacturing, since registration among the apertures is required in two dimensions.

As provided previously, at least one embodiment relates in general to configuring a diagnostic radiology X-ray device, system or apparatus (similar to one or more of those embodiments discussed previously) adapted to perform a diagnostic radiological scan, forming at least one image of an object having enhanced contrast. More particularly, one or more embodiments are directed to an X-ray device, system or apparatus having a flat panel detector portion (similar to the those provided previously) adapted to be configured as at least one of scintillator, direct configuration, or hybrid of the two. In at least one embodiment, one or more areas or portions of the flat panel detector (behind the pre-patient collimator for example and depicted as shaded areas in the figures) may be used as dead space for interconnects or as active pixels to measure scatter. Further, the removable post-patient collimator may be optimized to reject scatter between active pixel runs, but allow scatter in the shadowed pixels, enabling measurement of scattered images beam portions.

In at least one embodiment, a flat panel portion of the X-ray device, system or apparatus is configurable for at least one of standard scintillation, direct conversion and a hybrid of scintillation and direct conversion. The flat panel portion may include a detector anti-scatter grid adapted to reduce scatter and enhance contrast. A configuring device (an FET switch and scanning architecture for example) enables using all the data line read electronics only for the data rows exposed by the slot pre-patient collimator with selected channels dedicated to measuring the scatter from the channels shadowed by the pre-patient collimator. The flat panel detector (a multiplexed readout for example) may be configured in various configurations. The flat panel may be configured as a standard scintillator with all lines active and read as a standard flat panel. Alternatively, the flat panel detector may be configured using a multiplexed flat panel with rows of single crystal direct conversion material behind the pre-patient slots. Such a multiplexed flat panel may be configured as a dedicated slot scanner configuration, but may also be able to operate as a photon counting, energy discriminating detector at high kVs. In this embodiment, one or more of the direct conversion strips may be separated by a predetermined distance to minimize scatter (where each strip may be several pixel rows wide), and a mixed panel with some standard scintillator and some direct conversion rows.

At least one embodiment of the device, system or apparatus may include a source to image distance (alternatives SID) that may be modified. In this embodiment, as long as the ratio of source to pre-patient collimator/source to image (alternatively SPC/SI) remains constant. In at least one embodiment, a support (a mechanized support for example) may be used to maintain the SPC/SI as the SID is changed or modified.

At least one embodiment comprises a device, system or apparatus configured as a slot system where the SID is variable, but having at least one of the focal spot, pre-patient grid, and detector remain focused and aligned. This configuration may be achieved using a support that retains a constant ratio of SPC/SI as the SID is changed. Various configurations are contemplated for scanning the beam and designing the collimator slots. In at least one embodiment, at least one of the beam width, spacing and size of the slots could vary over the field of view, tailoring scatter contribution (customizing the IQ/Dose over the FOV). One or more slots could be holes (in any pattern) and motion could be in 2D slots. For example, the slots could be concentric circles and the scanning mechanism is changing tube to detector distance (or fixed tube to detector distance, but changing tube to patient distance).

In one embodiment, the flat panel detector portion, depicted in FIG. 6, comprises at least a standard scintillator or direct conversion flat panel detector, generally designated 600, having lines 650. In this embodiment, all lines 650 are active. In at least one embodiment, one or more lines 652 are adapted to detect direct radiation, while the other data lines 654 are adapted to measure scatter (perhaps for diffraction or scatter imaging).

Figure 7:
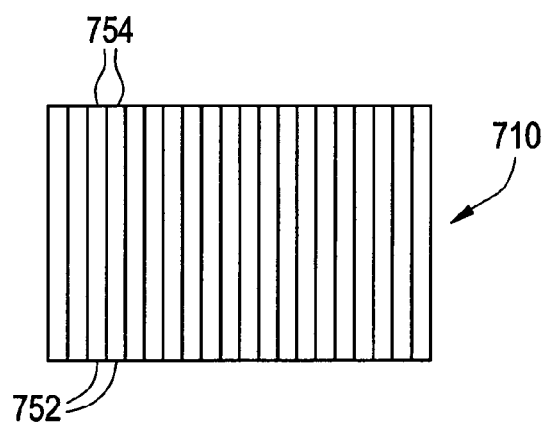
FIG. 7 depicts a flat panel detector having active lines separated at the frequency of the pre-patient collimator in accordance with certain embodiments of the present invention.

In at least one embodiment of the flat panel detector depicted in FIG. 7, generally designated 700, comprises at least two active stripes 752 separated at the frequency of the pre-patient collimator. These active stripes may contain one or more active lines of detector elements. The dead space 764 between the active lines 754 may be used for connections and packaging. This embodiment may be especially useful for detector rows comprised of single crystal direct conversion material. In this configuration, the areas between the primary detector rows (i.e., dead space 754) may have one or more active rows to measure scatter.

Figure 8:
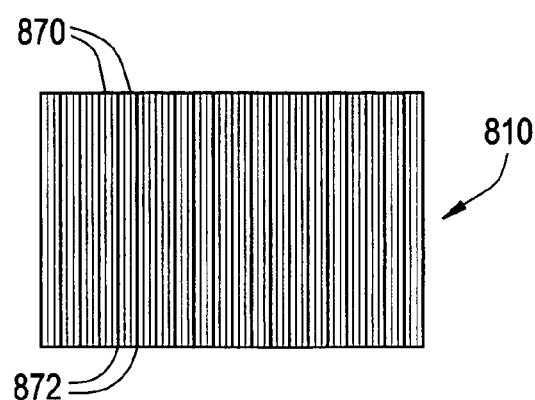
FIG. 8 depicts a hybrid flat panel detector having direct conversion in one or more areas and scintillator rows in one or more areas in accordance with certain embodiments of the present invention.

In one embodiment, the flat panel detector, depicted in FIG. 8 and generally designated 800, is a hybrid configuration. In this embodiment, direct conversion in the one or more primary areas 870, and one or more scintillator rows 872 in the areas between.

Figure 10B:
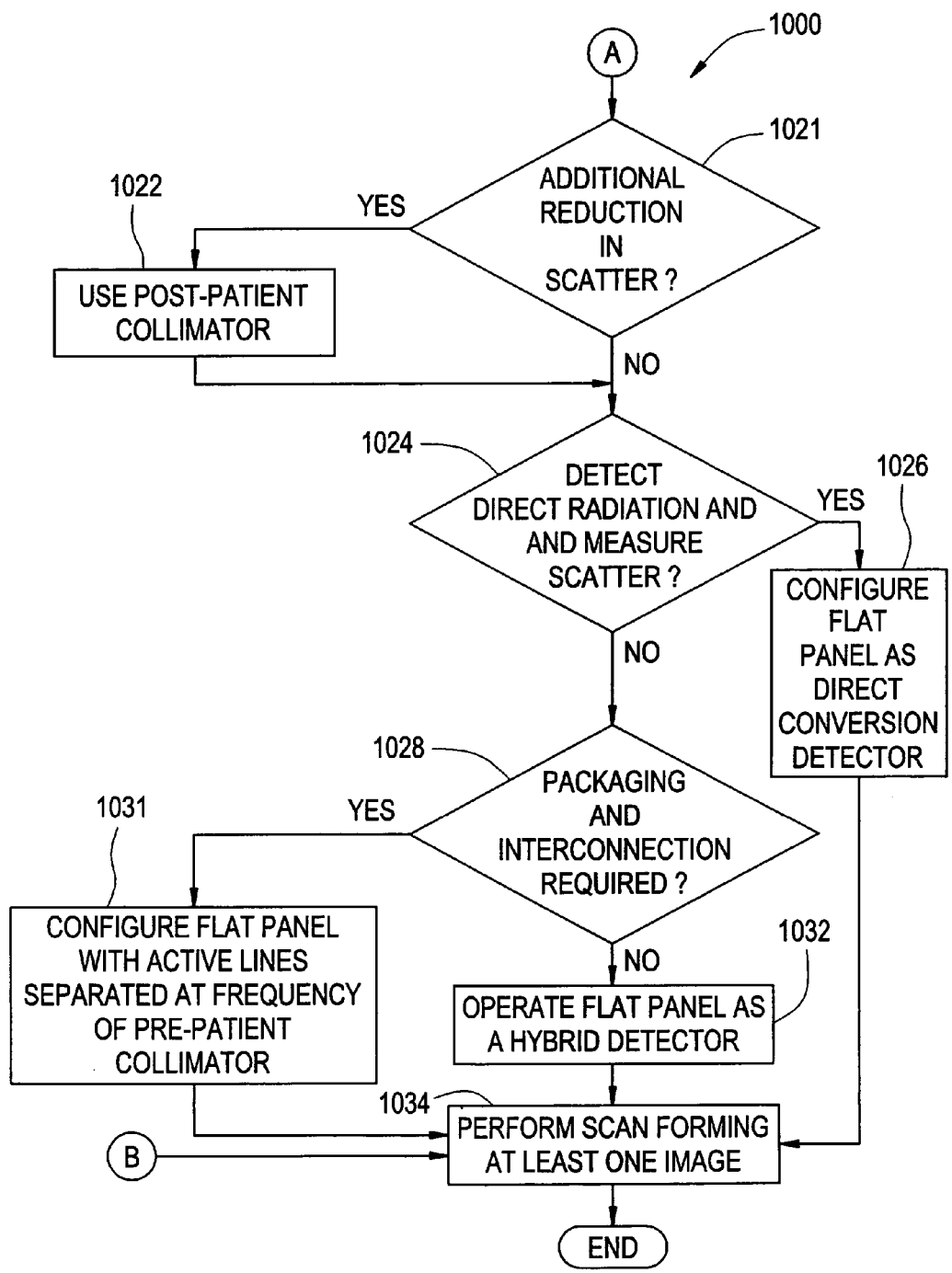

FIGS. 9, 10A and 10B depict flow diagrams illustrating methods of configuring a diagnostic radiology (X-ray) device, system or apparatus and forming at least one image using such a configured system in accordance with certain embodiments. One or more embodiments of the method comprise configuring scanning and flat panel detector portions of the system. At least one of these embodiments, configuring the scanning portion of the system, comprises configuring the scanning portion for at least one of high frame rate imaging and low dose imaging. As provided previously, configuring the scanning portion for high frame averaging comprises employing at least the removable pre-patient slot collimator, such that the system is employed as a slot scanner, achieving dose reduction benefits. Configuring the scanning portion for low dose imaging comprises not employing the removable pre-patient slot collimator, such that the system is employed in FOV mode, enabling fast image acquisitions (fluoro, tomo, cine, etc.).

In at least one of these embodiments, configuring the flat panel detector portion, comprises configuring the flat panel detector portion for at least one of measuring scatter, providing for interconnections and packaging, and a hybrid of measuring scatter and providing for interconnects. As provided previously, configuring the flat panel detector portion to measure scatter comprises configuring the flat panel detector as a standard scintillator or direct conversion flat panel, with all data lines active. One or more of the data lines would detect direct radiation, one or more of the other data lines would be used to measure scatter (for diffraction or scatter imaging for example). Configuring the flat panel detector portion to provide for interconnections and packaging comprises configuring the flat panel detector having at least two active data lines separated at the frequency of the pre-patient collimator. The dead space between the active data lines may be used for interconnections and packaging. This configuration may comprise detector rows comprised of single crystal direct conversion material. Further, in this configuration, the areas between the primary detector rows may have one or more active rows to measure scatter. Configuring the flat panel detector portion as a hybrid configuration comprises configuring the flat panel having direct conversion in the primary areas and scintillator rows in one or more areas between such primary areas.

FIG. 9 depicts a detailed high level flow diagram depicting a method of configuring a diagnostic radiology (X-ray) device, system or apparatus and forming at least one image using such configured system in accordance with certain embodiments. The method illustrated in FIG. 9, generally designated 900, comprises determining to perform a scan, Block 910. After determining to perform the scan, method 900 comprises configuring scanning and flat panel detector portions of the system, Blocks 920 and 930 respectively. In at least one embodiment, configuring the scanning portion of the apparatus, Block 920, comprises configuring the scanning portion for at least one of high frame rate imaging and low dose imaging. As provided previously, configuring the scanning portion for high frame averaging comprises employing at least the removable pre-patient slot collimator, such that the system is employed as a slot scanner, achieving dose reduction benefits. Configuring the scanning portion for low dose imaging comprises not employing the removable pre-patient slot collimator, such that the system is employed in FOV mode, enabling fast image acquisitions (fluoro, tomo, cine, etc.).

In at least one embodiment, configuring the flat panel detector portion, Block 930, comprises configuring the flat panel detector portion for at least one of standard scintillation, direct conversion and a hybrid of scintillation and direct conversion. As provided previously, configuring the flat panel detector portion as a standard scintillator comprises configuring the flat panel detector having all data lines active. One or more of the data lines may detect direct radiation, one or more of the other data lines may be used to measure scatter (perhaps for diffraction or scatter imaging). Configuring the flat panel detector portion to provide for interconnections and packaging comprises configuring the flat panel detector having at least two active data lines separated at the frequency of the pre-patient collimator. The dead space between the active data lines may be used for interconnections and packaging. This configuration may comprise one or more detector rows (comprised of single crystal direct conversion material for example). Further, in this configuration, one or more of the areas between the primary detector rows may have a few active rows to measure scatter. Configuring the flat panel detector portion as a hybrid configuration, comprising configuring the flat panel having direct conversion in one or more of the primary areas, and scintillator rows in one or more of the areas between the primary areas.

FIGS. 10A and 10B depict a detailed flow diagram depicting a method of configuring diagnostic radiology (X-ray) device, system or apparatus and forming at least one image using such configured system in accordance with certain embodiments. The method illustrated in FIGS. 10A and 10B, generally designated 1000, comprises deciding to perform a scan, Block 1010. In at least one embodiment, method 1000 comprises determining if low dose scanning is required, Diamond 1012. If low dose scanning is required, a removable pre-patient slot collimator is used or employed in the system, Block 1018, such that the system is employed in FOV mode, enabling fast image acquisitions (fluoro, tomo, cine, etc.). If low dose scanning is not required, method 1000 comprises determining if high frame rate imaging is required, Diamond 1014. If high frame rate imaging is required, the removable pre-patient slot collimator is not used, not employed or removed from the system, block 1016. As provided previously, configuring the scanning portion for high frame averaging provides dose reduction benefits.

At least one embodiment of method 1000 comprises determining if additional reduction in scatter is required, Diamond 1021. If additional reduction in scatter is required, at least one post-patient collimator may be used in the system, Block 1022. If additional reduction in scatter is not required, method 1000 comprises determining if detecting direct radiation and measuring scatter is required, Diamond 1024. If detecting direct radiation and measuring scatter is required, at least one embodiment of the flat panel may be operated as a standard scintillator or direct conversion detector having all data lines active, Block 1026. As such, a portion of the data lines would detect direct radiation, other data lines may be used to measure scatter (for example, for diffraction or scatter imaging).

It should be appreciated that configuring the flat panel detector as direct conversion, having active lines separated at the frequency of the pre-patient collimator or as a hybrid, 1026, 1031, 1032 may occur during design of the system. However, embodiments are contemplated in which such configuration may be selectable during operation.

In at least one embodiment, method 1000 comprises determining if space is required in the flat panel detector for interconnections and packaging, Diamond 1028. If such space is required, the flat panel detector is configured having two or more active data lines separated at the frequency of the pre-patient collimator, Block 1031. However, if such space is not required, the flat panel detector may be configured as a hybrid, Block 1032, having direct conversion in the primary areas, and scintillator rows in the areas between. Method 1000 further comprises performing a scan, forming at least one image using the configured system.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method of forming an image of an object using an X-ray device comprising:
    producing an X-ray beam using a conventional X-ray source;
    creating a plurality of beam segments from said X-ray beam;
    selecting between a scanning mode and a full field of view mode, wherein the scanning mode comprises scanning the object using at least one of said beam segments;
    producing an X-ray image on a flat panel detector.

2. The method of claim 1 comprising using a removable pre-patient collimator to form said plurality of beam portions.

3. The method of claim 1 comprising using a post-patient collimator passing at least one of said beam portion.

4. The method of claim 1 comprising minimizing acquisition time.

* * * * *